United States Patent [19]

Benzel et al.

[11] Patent Number: 5,713,900
[45] Date of Patent: Feb. 3, 1998

[54] APPARATUS FOR RETAINING BONE PORTIONS IN A DESIRED SPATIAL RELATIONSHIP

[75] Inventors: Edward C. Benzel, Albuquerque, N. Mex.; Hansen A. Yuan, Fayetteville, N.Y.; Alex Dinello, Palo Alto, Calif.; Michael H. Wefers, South Euclid, Ohio; Aaron C. Smith, Gibsonia, Pa.

[73] Assignee: AcroMed Corporation, Cleveland, Ohio

[21] Appl. No.: 656,398

[22] Filed: May 31, 1996

[51] Int. Cl.⁶ .................................................. A61B 17/70
[52] U.S. Cl. ............................ 606/61; 606/60; 606/72; 606/73
[58] Field of Search ............................ 606/60, 61, 72, 606/73

[56] References Cited

U.S. PATENT DOCUMENTS

| | | |
|---|---|---|
| 2,699,774 | 1/1955 | Livingston . |
| 4,041,939 | 8/1977 | Hall . |
| 4,484,570 | 11/1984 | Sutter et al. . |
| 5,024,213 | 6/1991 | Asher et al. . |
| 5,147,360 | 9/1992 | Dubousset . |
| 5,152,303 | 10/1992 | Allen . |
| 5,261,911 | 11/1993 | Carl . |
| 5,290,288 | 3/1994 | Vignaud et al. . |
| 5,395,371 | 3/1995 | Miller et al. . |
| 5,403,314 | 4/1995 | Currier . |
| 5,423,826 | 6/1995 | Coates et al. . |
| 5,474,555 | 12/1995 | Puno et al. . |
| 5,480,401 | 1/1996 | Navas . |
| 5,486,176 | 1/1996 | Hildebrand et al. . |
| 5,498,263 | 3/1996 | DiNello et al. .................. 606/61 |

OTHER PUBLICATIONS

*Sofamor Instrumentacion*, C.D. Hope, (8 pp.) Mar., 1994.
*Alpha Plaques Cervicales*, Stryker® Implants (2 pp.) Prior May 1996.
*Cervical Spine Locking Plate*, Original Instruments and Implants of the Association for the Study of Internal Fixation AO/ASIF, (7 pp.) Prior May 1996.

*Primary Examiner*—Michael Buiz
*Assistant Examiner*—Daphna Shai
*Attorney, Agent, or Firm*—Tarolli, Sundheim, Covell, Tummino & Szabo

[57] ABSTRACT

An apparatus for retaining first and second bone portions in a desired spatial relationship comprises a first member positionable along the first and second bone portions. A second member connectable with the first bone portion has surface member defining an opening. A fastener is extendable through the opening in the second member to connect the second member to the first bone portion. The fastener has a first portion for engaging the first bone portion and a second portion for clamping the first member against the second member to fix the first and second members against relative movement. The first member is also connected to the second bone portion.

8 Claims, 6 Drawing Sheets

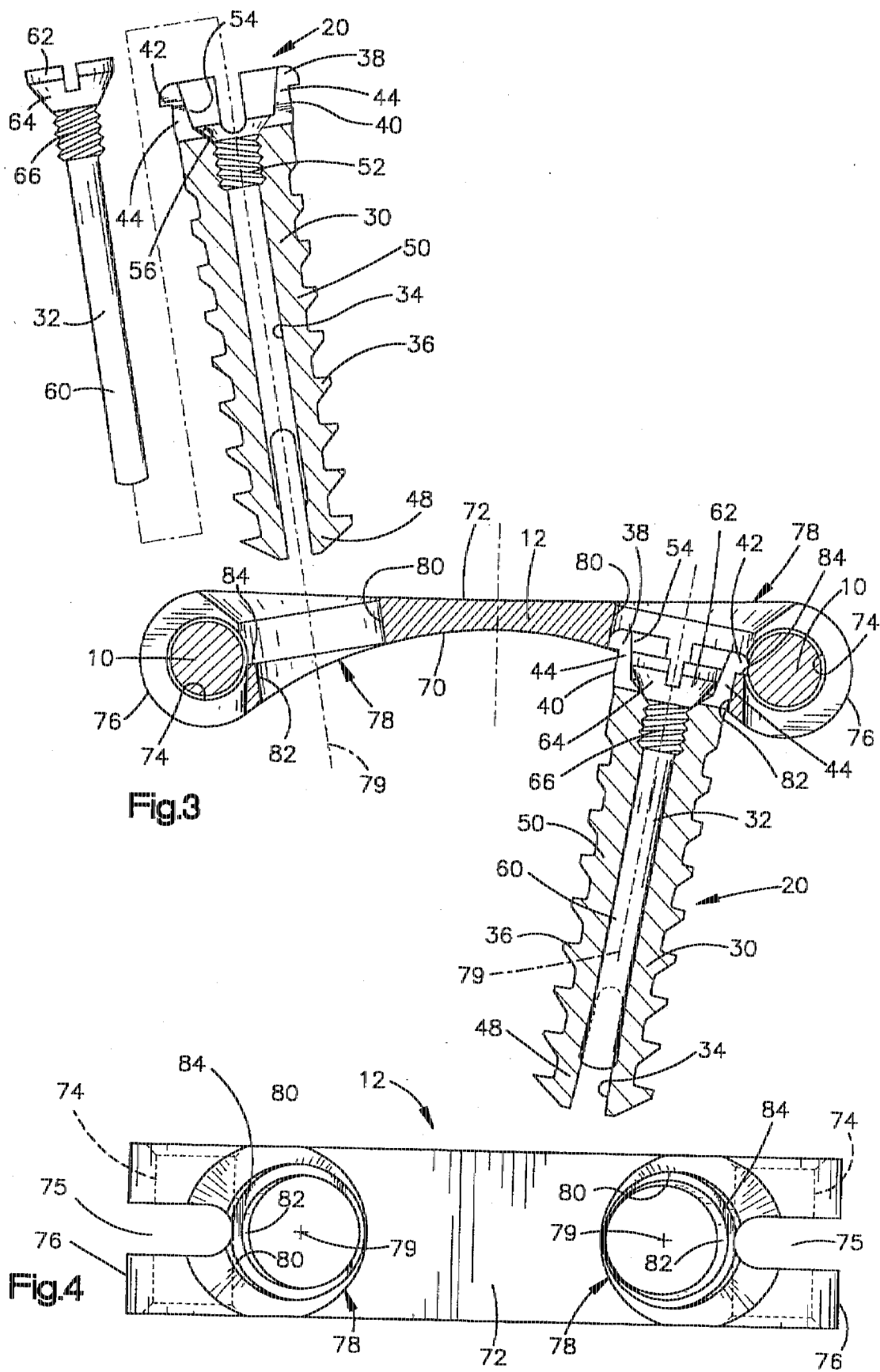

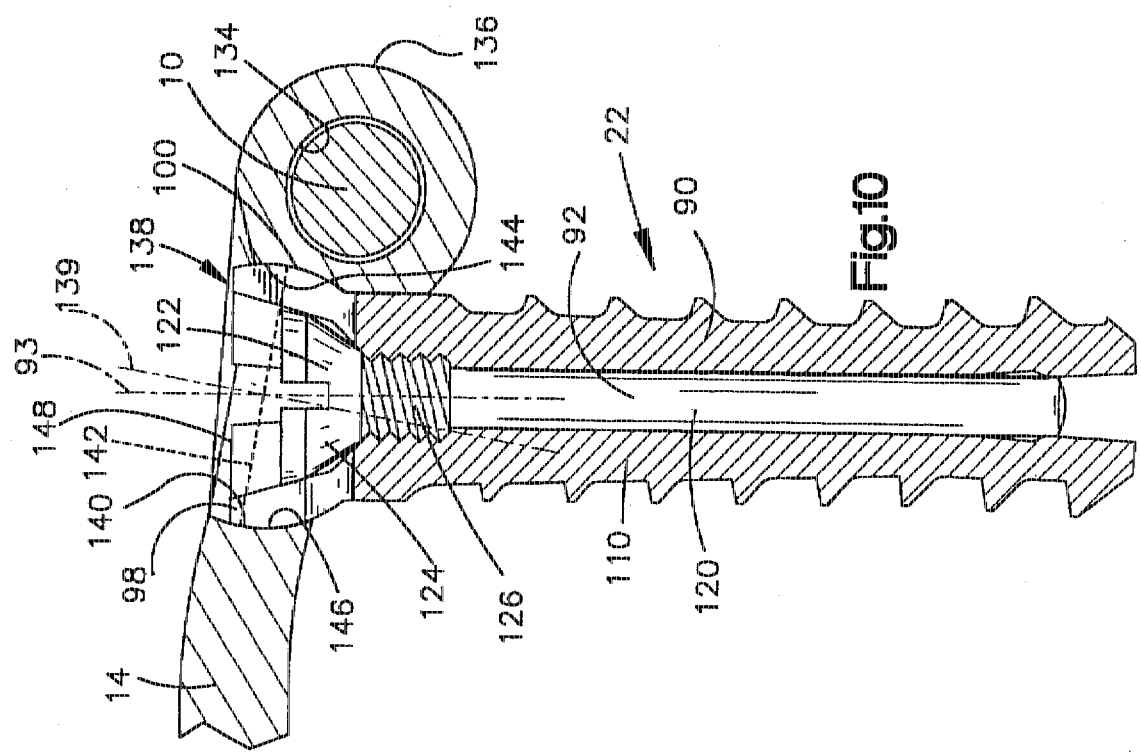
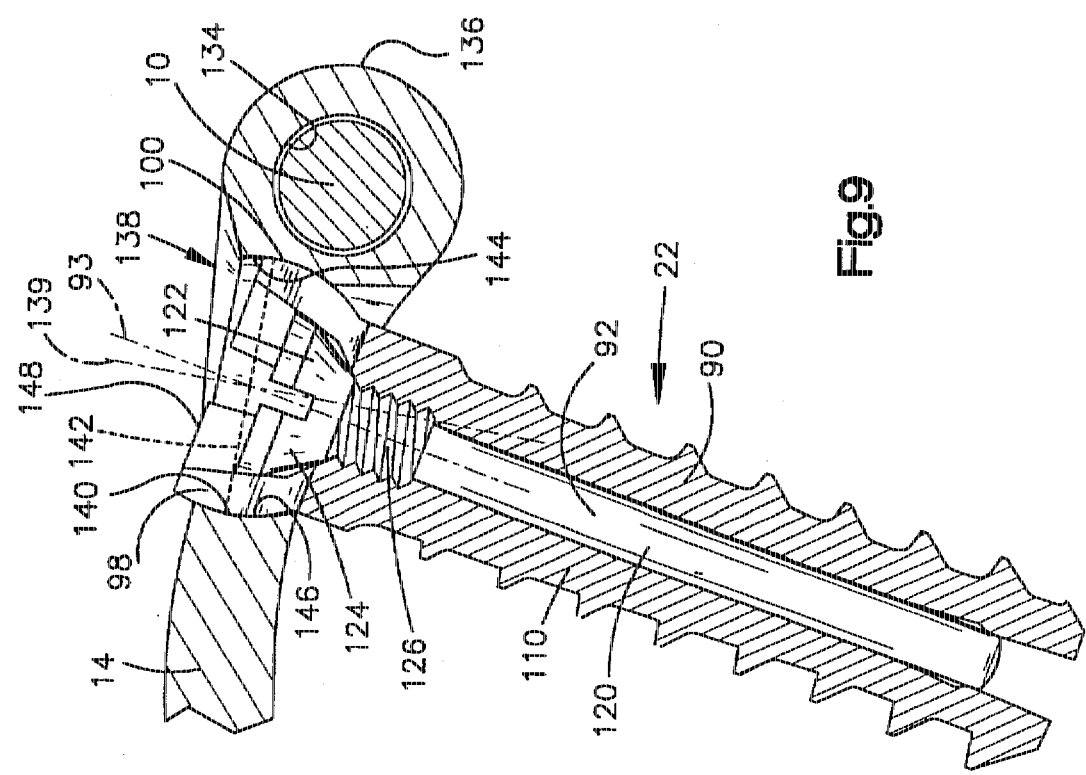

APPARATUS FOR RETAINING BONE PORTIONS IN A DESIRED SPATIAL RELATIONSHIP

BACKGROUND OF THE INVENTION

1. Technical Field

The present invention relates to an apparatus for use in retaining bone portions in a desired spatial relationship. Specifically, the present invention relates to an apparatus for connection to anterior portions of cervical vertebrae of a spinal column for retaining the cervical vertebrae in a desired spatial relationship.

2. Description of the Prior Art

There are various known apparatuses for retaining vertebrae of a spinal column in a desired spatial relationship. Certain of such known apparatuses include rods connected to and extending between vertebrae and certain of such known apparatuses include plates connected to and extending between vertebrae.

SUMMARY OF THE INVENTION

The present invention is an apparatus for retaining first and second bone portions, such as cervical vertebrae of a spinal column, in a desired spatial relationship. The apparatus includes a first member, preferably a longitudinally extending member such as a rod, positionable along the first and second bone portions. A second member, preferably a plate, connectable with the first bone portion has surface means defining an opening. A fastener is extendable through the opening in the second member to connect the second member to the first bone portion.

In accordance with one feature of the present invention, the fastener has a first portion for engaging the first bone portion and a second portion for clamping the first member against the second member to fix the first and second members against relative movement. Preferably, the fastener has a threaded portion which threads into the first bone portion and a head portion which is expandable to clamp the first member against the second member. The apparatus further includes means for connecting the first member to the second bone portion.

BRIEF DESCRIPTION OF THE DRAWINGS

The foregoing and other features of the present invention will become more apparent to one skilled in the art upon reading the following description of the invention with reference to the accompanying drawings, wherein:

FIG. 3 is an enlarged exploded view of parts of FIG. 1;

FIG. 4 is a plan view of a part shown in FIG. 3;

FIG. 9 is an enlarged view, generally similar to FIG. 8, showing another position of the parts of FIG. 8;

FIG. 10 is an enlarged view, generally similar to FIG. 8, showing yet another position of the parts of FIG. 8.

DESCRIPTION OF THE PREFERRED EMBODIMENTS OF THE INVENTION

Figure 1:
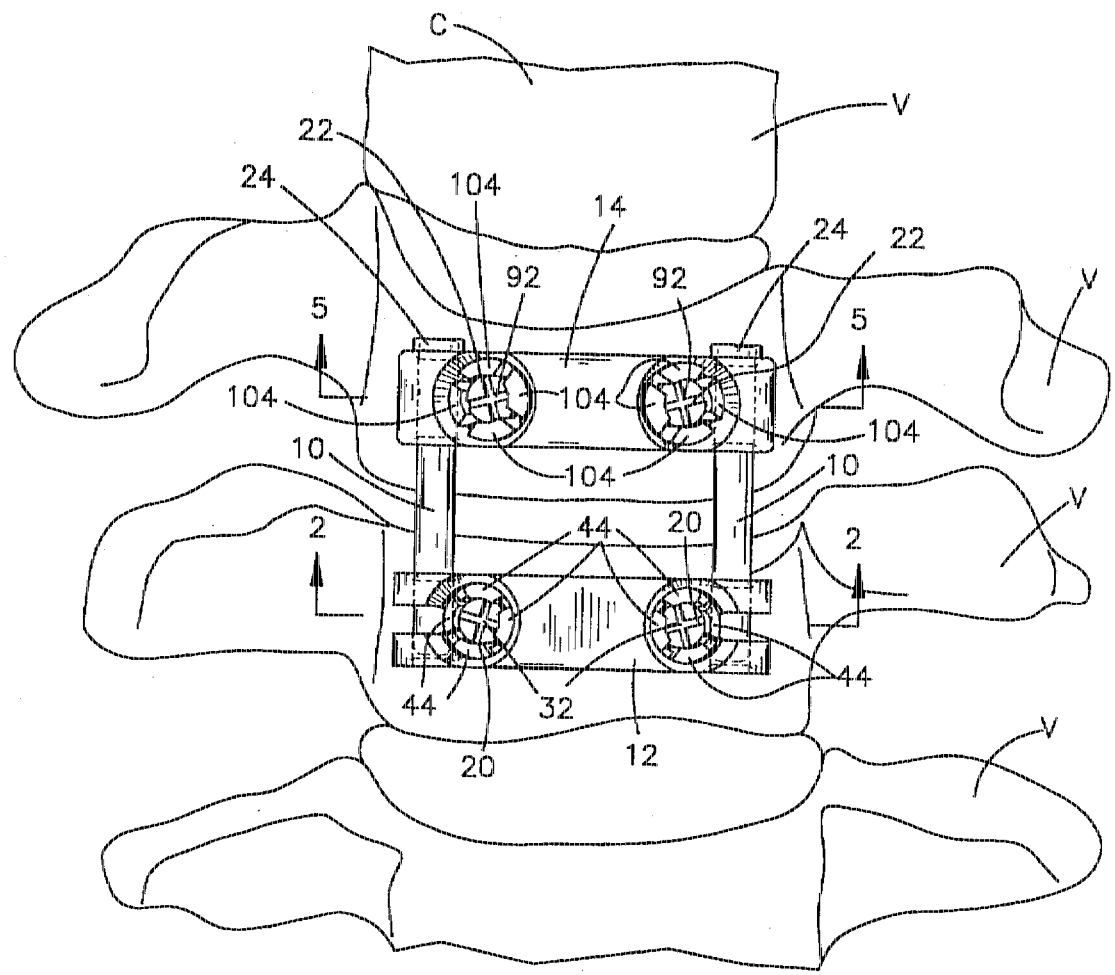
FIG. 1 is a view of a cervical portion of a spinal column with a first embodiment of an apparatus constructed in accordance with the present invention connected to anterior portions of the cervical vertebrae to retain a desired spatial relationship between the cervical vertebrae.

A pair of surgically implantable longitudinally extending members, such as rods 10, of a first embodiment of the present invention (FIG. 1) for correcting deformation and/or degeneration of a human spinal column C are connected to anterior portions of cervical vertebrae V of the spinal column by members in the form of plates 12 and 14. Each rod 10 is elongate and has a circular cross section taken in a plane extending perpendicular to the longitudinal central axis of the rod. The rods 10 are bendable in any desired plane to conform to a desired curvature of the spinal column C. The rods 10 have sufficient strength and rigidity to maintain the vertebrae V in the desired relationship. The rods 10 are made of a biocompatible material such as titanium or stainless steel.

Each of the rods 10 has a length which is at least sufficient to enable the rod to span at least two of the cervical vertebrae V. In the embodiment of the invention illustrated in FIG. 1, the rods 10 span two vertebrae V. Of course, the length of the rods 10 will depend upon the condition to be corrected and the number of vertebrae V to be held in a desired spatial relationship relative to each other by the rods 10.

Figure 2:
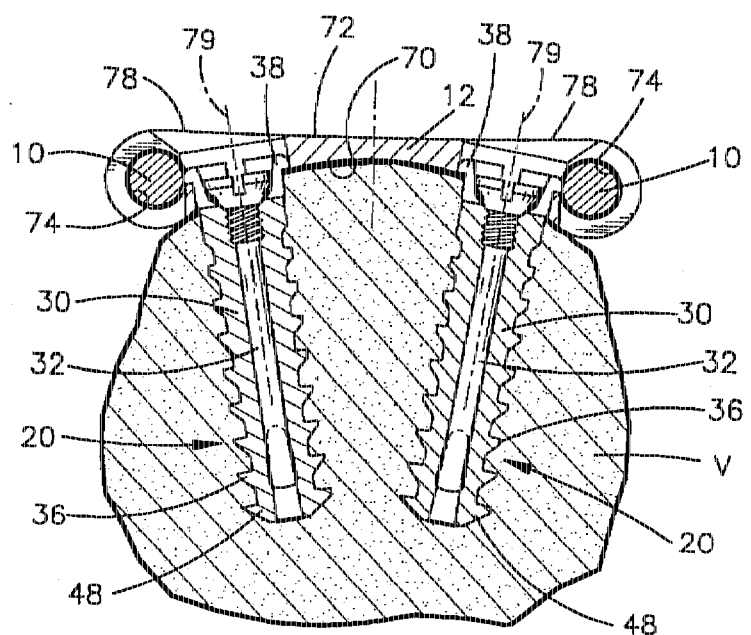
FIG. 2 is a sectional view, taken generally along the line 2—2 of FIG. 1.
Figure 5:
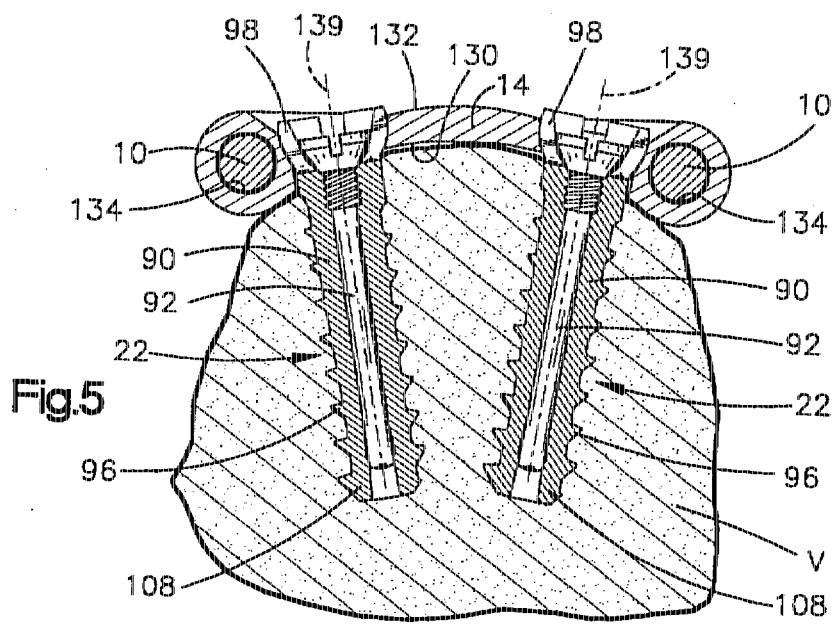
FIG. 5 is a sectional view, taken generally along the line 5—5 of FIG. 1.

The plate 12 is connected to a vertebra V by fasteners 20 (FIG. 2). The fasteners 20 also fix or lock the rods 10 relative to the plate 12 to prevent relative movement between the rods 10 and the plate. The plate 14 is connected to a vertebra V by fasteners 22 (FIG. 5). The fasteners 22 permit relative movement between the plate 14 and the rods 10. Therefore, the plate 14 is considered a dynamic plate.

Each rod 10 terminates in a cap 24 engageable with the plate 14. The caps 24 prevent movement of the plate 14 relative to the rods 10 in a direction away from the plate 12, while allowing movement of the plate 14 in a direction toward the plate 12.

Each of the fasteners 20 (FIGS. 2 and 3) includes a sleeve 30 and an expander 32 located within the sleeve. The sleeve 30 has an axially extending central opening 34 for receiving the expander 32. The sleeve 30 includes a coarse external helical thread convolution 36 for engaging a vertebra V.

The sleeve 30 (FIG. 3) has a head end portion 38 with a cylindrical outer side surface 40. An annular lip or rim 42 extends around the head end portion 38 of the sleeve 30 and projects radially outward from the cylindrical outer side surface 40. The head end portion 38 of the sleeve 30 is radially and axially slotted to define four segments 44 (FIG. 1) of the head end portion 38. The four segments 44 are movable radially outward relative to each other. Thus, the head end portion 38 is expandable. The radially and axially extending slots in the head end portion 38 receive a driving tool for threading the sleeve 30 into a vertebra. An end portion 48 (FIG. 3) of the sleeve 30 opposite from the head end portion 38 is radially and axially slotted to permit radially outward expansion of the end portion 48.

The opening 34 of the sleeve 30 has a first diameter located along a central portion 50 of the sleeve 30 and a second diameter smaller than the first diameter located adjacent the end portion 48. The sleeve 30 has an internally threaded portion 52 between the central portion 50 and the head end portion 38. The head end portion 38 has a conical shaped surface 54 that tapers from a larger diameter to a smaller diameter adjacent another conical shaped surface 56. The surface 56 interconnects the surface 54 and the threaded portion 52. The surface 56 tapers from a larger diameter adjacent of the surface 54 to the smaller diameter of the threaded portion 52.

The expander 32 has a rod portion 60 for extending in the opening 34. The rod portion 60 has a diameter which is approximately equal to the diameter of the opening 34 in the central portion 50 of the sleeve. The rod portion 60 engages the interior of the end portion 48 of the sleeve 30 and causes the end portion 48 to expand and help retain the fastener 20 in the vertebra V.

The expander 32 has a head end portion 62 with an X-shaped driver slot for receiving a driving tool for rotating the expander relative to the sleeve 30. The head end portion 62 has a tapering surface 64 for engaging the tapering surface 54 of the sleeve 30. The expander 32 includes a threaded portion 66 for threadably engaging the threaded portion 52 of the sleeve 30. The tapering surface 64 of the expander 32 engages the tapering surface 54 of the sleeve 30 to move the four segments 44 radially outward. Therefore, the head end portion 38 of the sleeve 30 expands.

The member or plate 12 (FIGS. 2–4) is made of a suitable biocompatible material, such as titanium or stainless steel. The plate 12 includes a surface 70 for engaging an anterior surface of the vertebra V and a surface 72 opposite from the surface 70 for facing away from the vertebra V. The plate 12 has generally parallel rod openings 74 for receiving the rods 10. Slots 75 (FIG. 4) extend from side surfaces 76 of the plate 12 and intersect the openings 74. The slots 75 define a pair of axially spaced arcuate surfaces that engage portions of the rod 10 at axially spaced locations.

The plate 12 (FIGS. 3 and 4) has a pair of fastener openings 78 for receiving the fasteners 20. The fastener openings 78 are located adjacent to and intersect, or overlap, the rod openings 74. The openings 78 have axes 79 that extend at an angle relative to each other so that the fasteners 20 extend at an angle to each other when the fasteners are connected with the plate 12.

Each one of the fastener openings 78 is partially defined by a larger diameter cylindrical surface 80 which extends parallel to the axis of the fastener openings. The fastener opening 78 is partially defined by a smaller diameter cylindrical surface 82 which extends parallel to the axis of the openings 78. An annular shoulder surface 84 extends radially between the surfaces 80 and 82. The shoulder surface 84 defines a seat or recess in the opening 78 against which the rim 42 of the sleeve 30 engages.

When the plate 12 is to be connected to the anterior portion of the cervical vertebra V, it is positioned on the anterior portion of the cervical vertebra with the surface 70 facing the anterior portion of the vertebra V and the rods 10 extending through the openings 74. The sleeves 30 of the fasteners 20 are placed through the fastener openings 78 in the plate 12 and threaded into the vertebra V. The sleeves 30 are threaded into the vertebra V until the rims 42 of the sleeves engage the shoulder surfaces 84 and press the surface 70 of the plate 12 against the vertebra V. The expanders 32 are threaded into the sleeves 30 to cause the head end portions 38 to expand so that the segments 44 expand radially outward into engagement with the cylindrical surfaces 80 of the fastener openings 78 in the plate 12. The head end portions 38 of the sleeves 30 also expand into engagement with the rods 10 in the rod openings 74 and clamp the rods in the openings 74. Accordingly, the fasteners 20, the plate 12, and the rods 10 are prevented from moving relative to each other.

When the apparatus is positioned on the spinal column C, the fasteners 20 secure the plate 12 to its associated vertebra V. The plate 12 is also fixed in position relative to the rods 10, as described above. Accordingly, the vertebra V to which the plate 12 is connected is fixed in position relative to the rods 10.

Each of the fasteners 22 (FIGS. 5 and 6) which secure the plate 14 to a vertebra V includes a sleeve 90 and an expander 92 located within the sleeve. Each fastener 22 has a longitudinal central axis 93. The sleeve 90 has an axially extending central opening 94 for receiving the expander 92. The sleeve 90 includes a coarse external helical thread convolution 96 for engaging a vertebra V.

The sleeve 90 (FIG. 6) has a head end portion 98 with a part spherical outer side surface 100. The head end portion 98 of the sleeve 90 is radially and axially slotted to define four segments 104 (FIG. 1) of the head end portion 98. The four segments 104 are movable radially inward and outward relative to each other so that the head end portion 98 is expandable and collapsible. The radially and axially extending slots in the head end portion 98 receive a driving tool for threading the sleeve 90 into a vertebra V. An end portion 108 (FIG. 6) of the sleeve 90 opposite from the head end portion 98 is radially and axially slotted to permit radially outward expansion of the end portion 108. The head end portion 98 of the sleeve 90 has a surface 148 facing away from the end portion 108.

The opening 94 of the sleeve 90 has a first diameter located along a central portion 110 of the sleeve 90 and a second diameter smaller than the first diameter located adjacent the end portion 108. The sleeve 90 has an internally threaded portion 112 between the central portion 110 and the head end portion 98. The head end portion 98 has a conical shaped surface 114 that tapers from a larger diameter to a smaller diameter adjacent another conical shaped surface 116. The surface 116 interconnects the surface 114 and the threaded portion 112. The surface 116 tapers from a larger diameter adjacent the surface 114 to the smaller diameter of the threaded portion 112.

The expander 92 has a rod-shaped portion 120 for extending into the opening 94. The rod portion 120 has a diameter which is approximately equal to the diameter of the opening 94 in the central portion 110 of the sleeve 90. The rod portion 120 engages the interior of the end portion 108 of the sleeve 90 and causes the end portion 108 to expand and help retain the fastener 22 in the vertebra V.

The expander 92 has a head end portion 122 with an X-shaped driver slot for receiving a driving tool for rotating the expander relative to the sleeve 90. The head end portion 122 has a tapering surface 124 for engaging the tapering surface 114 of the sleeve 90. The expander 92 includes a threaded portion 126 for threadably engaging the threaded portion 112 of the expander 90. The tapering surface 124 of the expander 92 engages the tapering surface 114 of the sleeve 90 to move the four segments 104 radially outward. Therefore, the head end portion 98 of the sleeve 90 expands.

The member or plate 14 (FIGS. 5–7) is made of a suitable biocompatible material, such as titanium or stainless steel. The plate 14 includes a surface 130 for engaging an anterior surface of the vertebra V and a surface 132 opposite from the surface 130 for facing away from the vertebra V. The plate 14 has generally parallel rod openings 134 for receiving the rods 10.

The plate 14 has a pair of fastener openings 138 for receiving the fasteners 22. The fastener openings 138 are located adjacent to the rod openings 134 but do not intersect or overlap the rod openings 134. The fastener openings 138 have axes 139 extending at an angle to each other.

Figure 6:
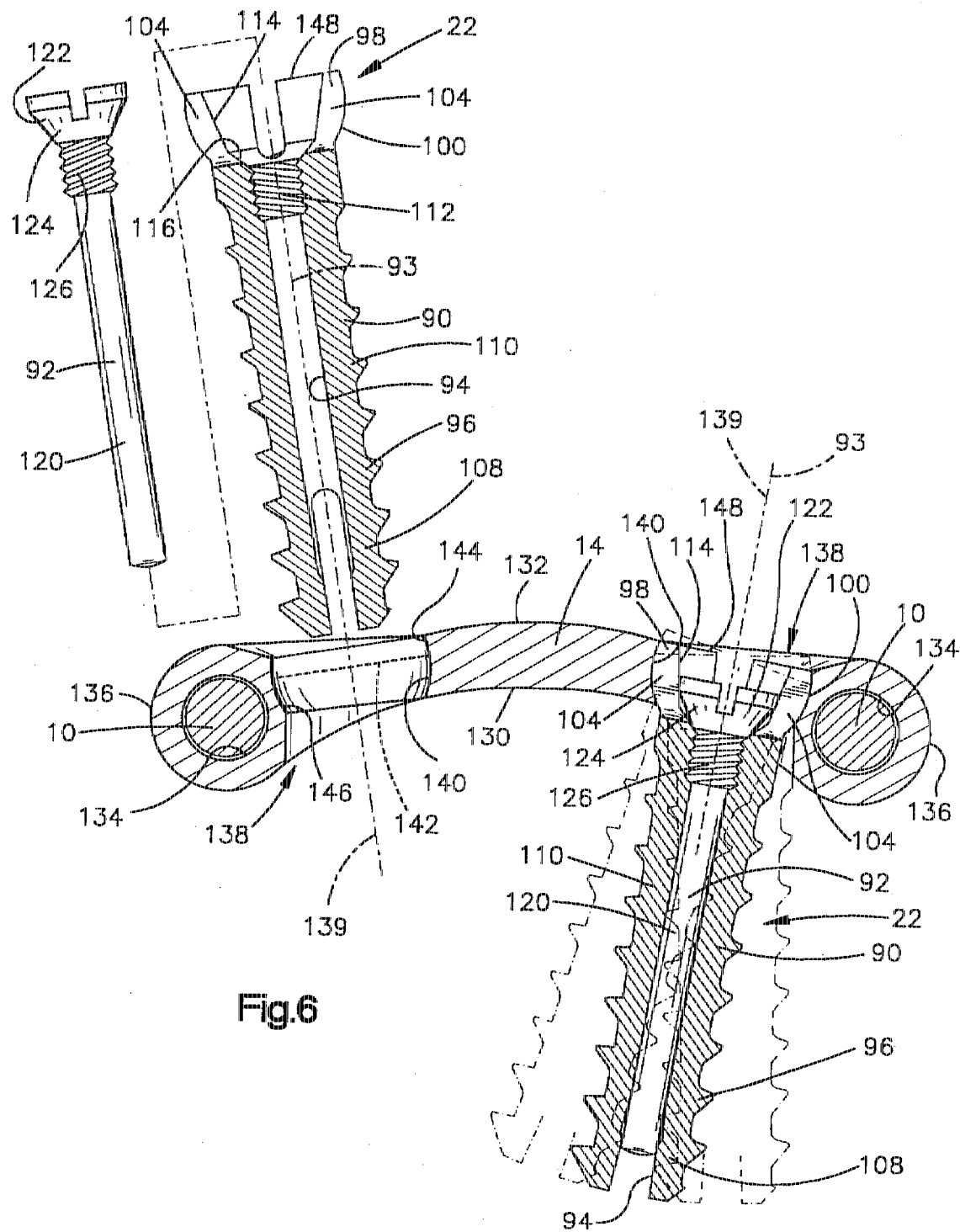
FIG. 6 is an enlarged exploded view of parts of FIG.
Figure 7:
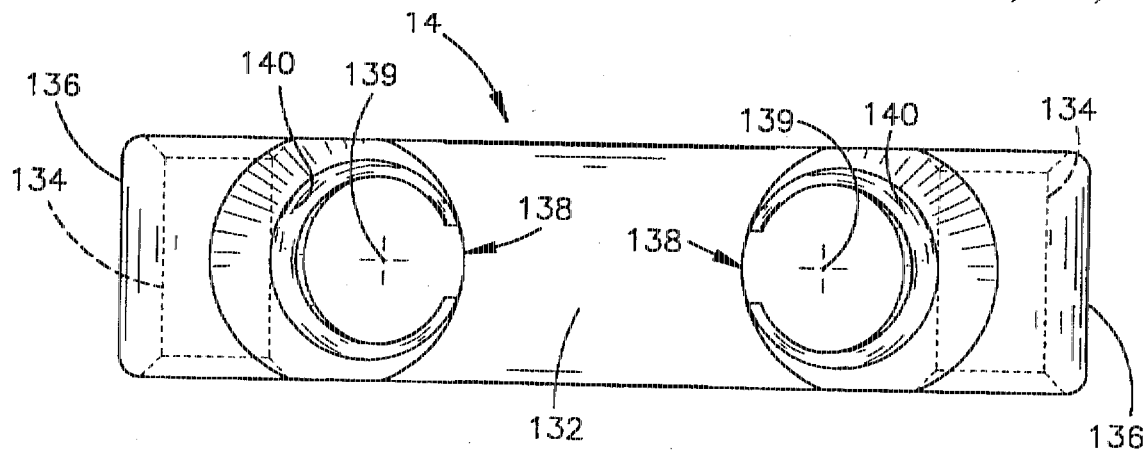
FIG. 7 is a plan view of a part shown in FIG. 6.
Figure 8:
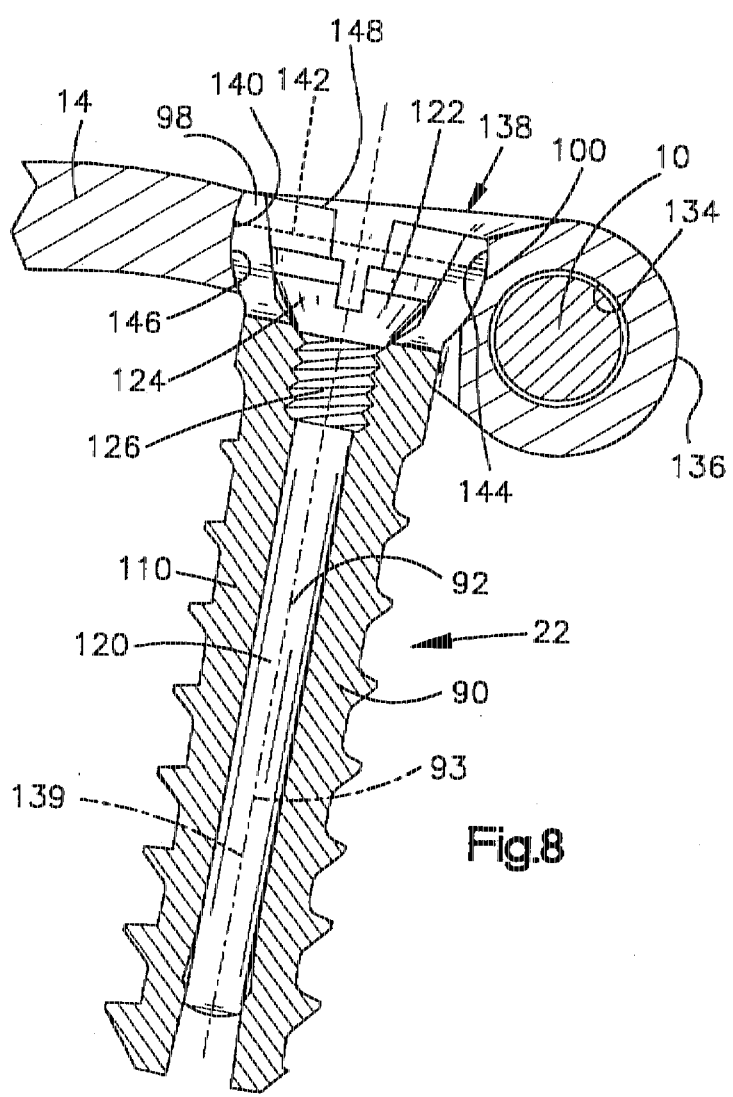
FIG. 8 is an enlarged view of parts of FIG. 6.

Each one of the fastener openings 138 is partially defined by a part spherical surface 140 (FIGS. 6–10) centered on the axis 139. The part spherical surface 140 defines a seat or recess in the opening 138 against which the part spherical surface 100 of the sleeve 90 is engageable. The part spherical recess 140 has a major diameter 142 (FIGS. 6 and 8). A first portion 144 of the recess 140 is located on one side of the major diameter 142 and adjacent the surface 132 of the plate 14. A second portion 146 of the recess 140 is located on the other side of the major diameter 142 and adjacent the surface 130 of the plate 14.

When the plate 14 is to be connected to a vertebra V, the plate 14 is placed on the vertebra V with the surface 130 engaging the anterior portion of the vertebra V and the rods 10 extending through the openings 134. The sleeves 90 are threaded into the vertebra V through the fastener openings 138 in the plate 14. As the head end portions 98 of the sleeves 90 enter the openings 138 in the plate 14, the segments 104 are compressed radially inward then expand radially outward. The surfaces 148 on the head end portions 98 of the sleeves 90 are located in the first portions 144 of the recesses 140 when the head end portions 98 are received in the recesses. Because the major diameter 142 of each recess 140 is spaced inward from the outer surface 132 of the plate 14, the expanded fasteners 22 resist movement out of the recesses in the plate.

The expanders 92 are threaded into the sleeves 90 and cause the head end portions 98 of the sleeves to expand into engagement with the openings 138 and prevent relative movement between the plate 14 and the fasteners 22.

The engagement of the part spherical surfaces 100 of the sleeves 90 with the part spherical surfaces 140 of the openings 138, enables the fasteners 22 to have a plurality of positions in which the axis 93 of each fastener 22 extends at an angle to the axis 139 of its associated opening 138 in any direction. Preferably, the axis 93 of each fastener 22 can be positioned at a maximum of approximately 10° in any direction relative to the axis 139 of its associated opening 138. Three alternative positions are shown in FIGS. 8–10.

The fasteners 22 secure the plate 14 to the vertebra V. However, the plate 14 is movable relative to the rods 10 because the fastener openings 138 do not intersect or overlap the rod openings 134. As a result, the vertebra V connected to the plate 14 is movable relative to the rods 10 along the longitudinal axes of the rods 10.

Accordingly, the vertebra V connected to the plate 14 is movable vertically downward toward the vertebra to which the plate 12 is connected. This relative movement allows for the maintaining of a load on bone graft placed between the vertebrae V. If the plate 14 was not movable relative to the plate 12, then the distance between the vertebrae V would be fixed. If a bone graft is placed between the vertebrae V and the bone graft resorbed sufficiently, the bone graft could possibly shrink out of engagement with one or both of the vertebrae V. Allowing relative movement of the plates 12 and 14 can help to maintain a desired load on bone graft placed between the vertebrae V and maintain the vertebrae in contact with the bone graft to facilitate bone growth.

It may not be necessary, in some circumstances, to use a dynamic (movable) plate such as the plate 14. In such circumstances, two plates identical to the plate 12 can be used in the same apparatus. Such a system is illustrated in FIG. 11.

Figure 11:
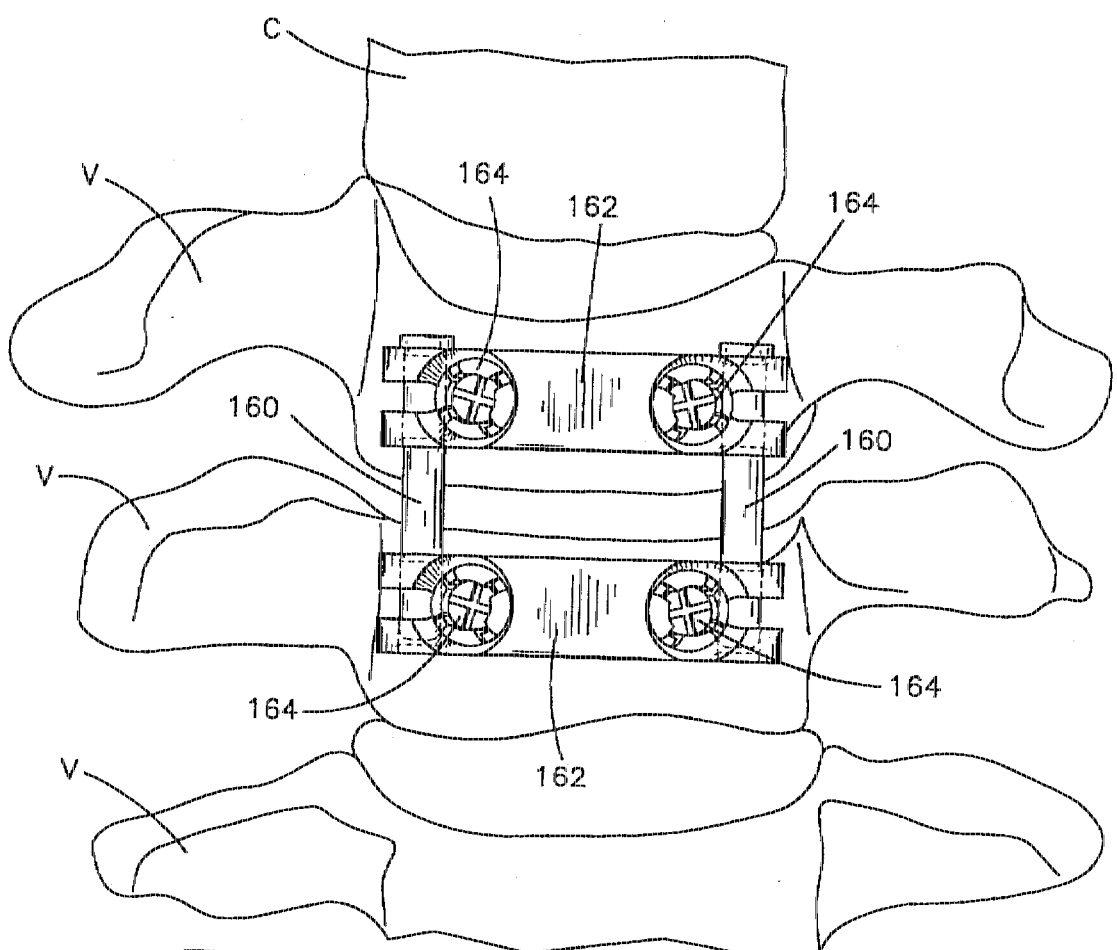
FIG. 11 is a view of a cervical portion of a spinal column with a second embodiment of an apparatus constructed in accordance with the present invention connected to anterior portions of the cervical vertebrae to retain a desired spatial relationship between the cervical vertebrae.

In FIG. 11 a pair of surgically implantable rods 160 are shown connected to anterior portions of cervical vertebrae V of a spinal column C by a pair of identical plates or members 162. The plates 162 are identical to the plates 12 illustrated in FIGS. 1–4 and will not be described in detail. The plates 162 are connected to the vertebrae V by fasteners 164. The fasteners 164 are identical to the fasteners 20 illustrated in FIGS. 1–3 and will not be described in detail. The fasteners 164 also fix the rods 160 relative to the plates 162 to prevent relative movement between the rods and the plates. The apparatus illustrated in FIG. 11 prevents relative movement between the vertebrae V since the plates 162 and rods 160 are prevented from moving relative to each other by the fasteners 164.

From the above description of the invention, those skilled in the art will perceive improvements, changes and modifications in the invention. Such improvements, changes and modifications within the skill of the art are intended to be covered by the appended claims.

Having described the invention, we claim the following:

1. An apparatus for retaining first and second bone portions in a desired spatial relationship, said apparatus comprising:

a first member positionable along the first and second bone portions;

a second member connectable with the first bone portion and having first surface means defining a first opening;

a first fastener extendable through said first opening in said second member to connect said second member to the first bone portion, said first fastener having a first portion for engaging the first bone portion and a second portion fixedly connected to said first portion with means for clamping said first member against said second member to fix said first and second members against relative movement; and means for connecting said first member to the second bone portion.

2. An apparatus as set forth in claim 1 wherein said second portion of said first fastener is expandable into engagement with said first surface means defining said first opening in said second member to prevent relative movement between said first fastener and said second member, said second portion of said first fastener also being expandable into engagement with said first member to clamp said first member against said second member, said first fastener including means for expanding said second portion of said first fastener into engagement with said first surface means defining said first opening and into engagement with said first member.

3. An apparatus as set forth in claim 2 wherein said second member includes a passage through which said first member is extendable, said passage intersecting said first opening through which said first fastener is extendable, said second portion of said first fastener extending into said passage to clamp said first member against said second member in said passage.

4. An apparatus as set forth in claim 1 wherein said first fastener includes a threaded sleeve for threadably engaging the first bone portion and an expander for expanding said second portion of said first fastener, said sleeve having surface means defining an axially extending opening into which said expander is extendable, said surface means defining said axially extending opening having a tapering surface engageable with a tapering surface on said expander to expand said second portion of said first fastener into engagement with said first surface means defining said first opening in said second member and into engagement with said first member to clamp said first member against said second member.

5. An apparatus as set forth in claim 1 wherein said first member is a first longitudinal member, said apparatus further including a second longitudinal member positionable along the spinal column generally parallel to said first longitudinal member and a second fastener for connecting said second member to the first bone portion, said second fastener being extendable through a second opening in said second member to connect said second member to the first bone portion, said second fastener having a first portion for engaging the first bone portion and a second portion fixedly connected to said first portion for clamping said second longitudinal member against said second member to fix said second member and said second longitudinal member against relative movement, said means for connecting said first member to the second bone portion including means for connecting said second longitudinal member to the second bone portion.

6. An apparatus as set forth in claim 5 wherein said second portion of said second fastener is expandable into engagement with second surface means defining said second opening in said second member to prevent relative movement between said second fastener and said second member, said second portion of said second fastener also being expandable into engagement with said second longitudinal member to clamp said second longitudinal member against said second member, said second fastener including means for expanding said second portion of said second fastener into engagement with said second surface means defining said second opening and into engagement with said second longitudinal member to clamp said second longitudinal member against said second member.

7. An apparatus as set forth in claim 5 wherein said means for connecting said first and second longitudinal members to the second bone portion includes a third member connectable with the second bone portion and having third and fourth surface means defining third and fourth openings, respectively, in said third member, and third and fourth fasteners extendable through said third and fourth openings in said third member to connect said third member to the second bone portion.

8. An apparatus as set forth in claim 7 wherein said third fastener has a first portion for engaging the second bone portion and a second portion, said second portion of said third fastener being expandable into engagement with said third surface means defining said third opening in said third member to prevent relative movement between said third fastener and said third member, said third fastener including means for expanding said second portion of said third fastener into engagement with said third surface means defining said third opening, said fourth fastener having a first portion for engaging the second bone portion and a second portion, said second portion of said fourth fastener being expandable into engagement with said fourth surface means defining said fourth opening in said third member to prevent relative movement between said fourth fastener and said third member, said fourth fastener including means for expanding said second portion of said fourth fastener into engagement with said fourth surface means defining said fourth opening.

* * * * *